(12) United States Patent
Lechmann et al.

(10) Patent No.: US 8,439,949 B2
(45) Date of Patent: May 14, 2013

(54) FACET JOINT AUGMENTATION WITH HYDROGELS

(75) Inventors: Beat Lechmann, Grenchen (CH); Robert Frigg, Bettlach (CH); Nigel Smith, Norwich (GB)

(73) Assignee: Synthes USA, LLC, West Chester, PA (US)

( * ) Notice: Subject to any disclaimer, the term of this patent is extended or adjusted under 35 U.S.C. 154(b) by 159 days.

(21) Appl. No.: 13/055,833

(22) PCT Filed: Jul. 24, 2009

(86) PCT No.: PCT/US2009/051661
§ 371 (c)(1), (2), (4) Date: Jan. 25, 2011

(87) PCT Pub. No.: WO2010/011904
PCT Pub. Date: Jan. 28, 2010

(65) Prior Publication Data
US 2011/0130764 A1    Jun. 2, 2011

Related U.S. Application Data

(60) Provisional application No. 61/083,622, filed on Jul. 25, 2008.

(51) Int. Cl.
*A61B 17/70* (2006.01)
(52) U.S. Cl.
USPC ............................... 606/247; 606/279

(58) Field of Classification Search ............. 606/92–94, 606/246–247; 623/17.12
See application file for complete search history.

(56) References Cited

U.S. PATENT DOCUMENTS

| | | | |
|---|---|---|---|
| 6,699,247 B2 | 3/2004 | Zucherman et al. | |
| 7,799,057 B2 * | 9/2010 | Hudgins et al. | 606/247 |
| 2005/0143818 A1 * | 6/2005 | Yuan et al. | 623/17.11 |
| 2006/0122704 A1 * | 6/2006 | Vresilovic et al. | 623/17.16 |
| 2007/0032790 A1 | 2/2007 | Aschmann et al. | |
| 2007/0118218 A1 * | 5/2007 | Hooper | 623/14.12 |
| 2007/0225706 A1 | 9/2007 | Clark et al. | |
| 2007/0225807 A1 | 9/2007 | Phan et al. | |
| 2007/0260245 A1 | 11/2007 | Malandain et al. | |
| 2008/0058937 A1 | 3/2008 | Malandain et al. | |
| 2008/0312744 A1 | 12/2008 | Vresilovic et al. | |

FOREIGN PATENT DOCUMENTS

| | | |
|---|---|---|
| WO | WO 2009/111632 | 9/2009 |
| WO | WO 2010/075451 | 7/2010 |

\* cited by examiner

*Primary Examiner* — Todd Manahan
*Assistant Examiner* — Jessica Weiss
(74) *Attorney, Agent, or Firm* — Stradley Ronon Stevens & Young, LLP

(57) ABSTRACT

A method for augmenting a facet joint. The method includes exposing the posterior aspects of a spinal motion segment in a first incision, preparing an access path through a separate postero-lateral percutaneous incision using a drilling instrument that traverses through at least a portion of the lamina and an inferior facet articulation surface, and terminates within the facet joint gap, and injecting augmentation filler into the facet joint gap.

15 Claims, 6 Drawing Sheets

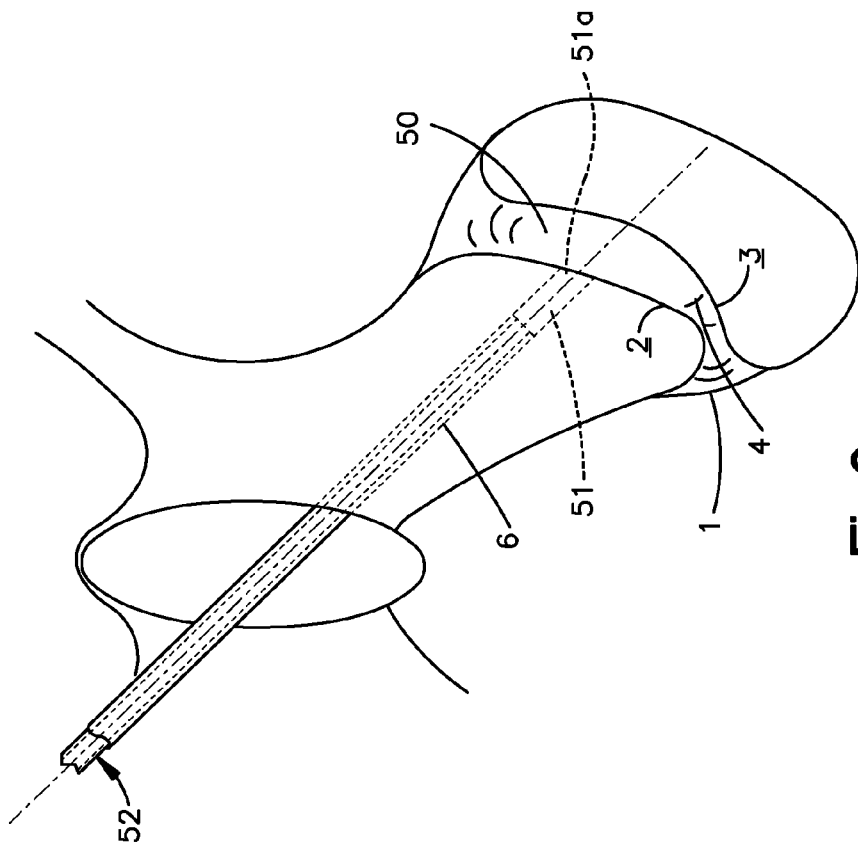
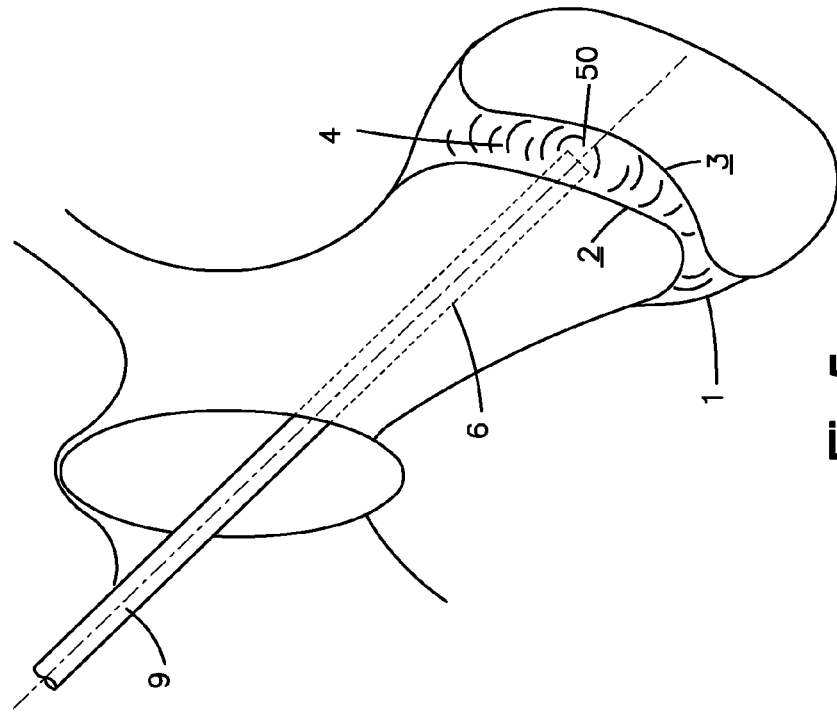

FACET JOINT AUGMENTATION WITH HYDROGELS

CROSS-REFERENCE TO RELATED APPLICATIONS

This application is the National Stage of International Application No. PCT/US2009/051661, filed Jul. 24, 2009, which claims the benefit of U.S. Provisional Application No. 61/083,622, filed Jul. 25, 2008, the disclosures of which are incorporated herein by reference in their entireties for all purposes.

BACKGROUND OF THE INVENTION

The facet joint is an articulating joint of a spinal motion segment that can degenerate during aging, trauma, typical use and other factors. The facet joints in various regions of the spine are oriented in different planes, for example, the lumbar facet joints are generally located in the sagittal plane, the thoracic facet joints are generally oriented in the coronal plane and the cervical facet joints are generally oriented in the axial or transverse plane. These orientations facilitate different types of motion in the respective regions of the spine.

Degenerated facet joints are often painful as a result of, for example, wear between two arthritic articulating surfaces contained within the synovial joint capsule. The surfaces of the facet joints are covered by articular cartilage. Inflammatory reactions may occur when the cartilaginous surfaces of the facets become degraded or fissured, thereby leading to direct bone-on-bone contact and resulting in pain. Over distraction of the surrounding joint capsules may also cause pain to a patient. Patients typically undergo a fusion surgery to alleviate this type of pain related to the facet which by its nature is invasive and nonreversible.

It is desirable to develop a non-invasive or minimally invasive system and method that can alleviate the pain resulting from degenerating facet joints.

SUMMARY OF THE INVENTION

The present invention relates generally to a method of facet joint augmentation using hydrogels or similar materials. More specifically, a preferred embodiment of the present invention relates to a method for augmenting a facet joint in a minimally invasive manner. The preferred method comprises exposing the posterior aspects of a spinal motion segment, preparing an access path through a postero-lateral percutaneous incision using a drilling instrument that traverses through at least a portion of the lamina and a superior facet articulation surface, and terminates within the facet joint gap, inserting an injection instrument through the access path, injecting augmentation filler into the facet joint gap in a liquid state, removing the injection instrument; and inserting a sealing material through the access path such that the terminal end of the sealing material is positioned generally coplanar with the superior facet articulation surface.

In one preferred embodiment the augmentation filler that is selected from the group consisting of hydrogels, ionomers, silicones or thermoplastic resins and can be pressurized by the insertion of the sealing member. In another preferred embodiment, the method further includes utilizing an image intensifier tool to enable proper insertion of the injection instrument. The sealing material is preferably a bone plug and is selected from the group consisting of allograft bone, hydroxyapatite or tri-calcium phosphate. The bone plug is preferably cylindrical in shape and has a similar diameter to the diameter of the access path.

In one preferred embodiment, the method for augmenting a facet joint in a minimally invasive manner, comprises creating an incision in a patient's back that exposes the posterior aspects of a spinal motion segment, creating a postero-lateral percutaneous incision to allow insertion of a drilling instrument, preparing an access path through the postero-lateral percutaneous incision using the drilling instrument which access path traverses through at least a portion of the lamina and a superior facet articulation surface, and terminates within the facet joint gap, inserting an injection instrument with augmentation filler through the access path, injecting the augmentation filler into the facet joint gap, removing the injection instrument; and inserting a sealing member through the access path such that the sealing member maintains pressure on the augmentation filler.

BRIEF DESCRIPTION OF THE DRAWINGS

The foregoing summary, as well as the following detailed description of preferred embodiments of the application, will be better understood when read in conjunction with the appended drawings. For the purposes of illustrating the preferred method of facet joint augmentation using hydrogels, there are shown in the drawings preferred embodiments. It should be understood, however, that the drawings are not intended to limit the scope of this invention, but merely to clarify and be illustrative of embodiments of the invention. In the drawings:

FIG. 5 illustrates a magnified posterior elevational view into an incision showing the injection of an augmentation filler into the facet joint gap according to the preferred embodiment of FIG. 2;

FIG. 6 illustrates a magnified posterior elevational view into an incision showing the closing or plugging of the access channel and injection opening according to the preferred embodiment of FIG. 2.

DETAILED DESCRIPTION OF CERTAIN EMBODIMENTS

Figure 1A:
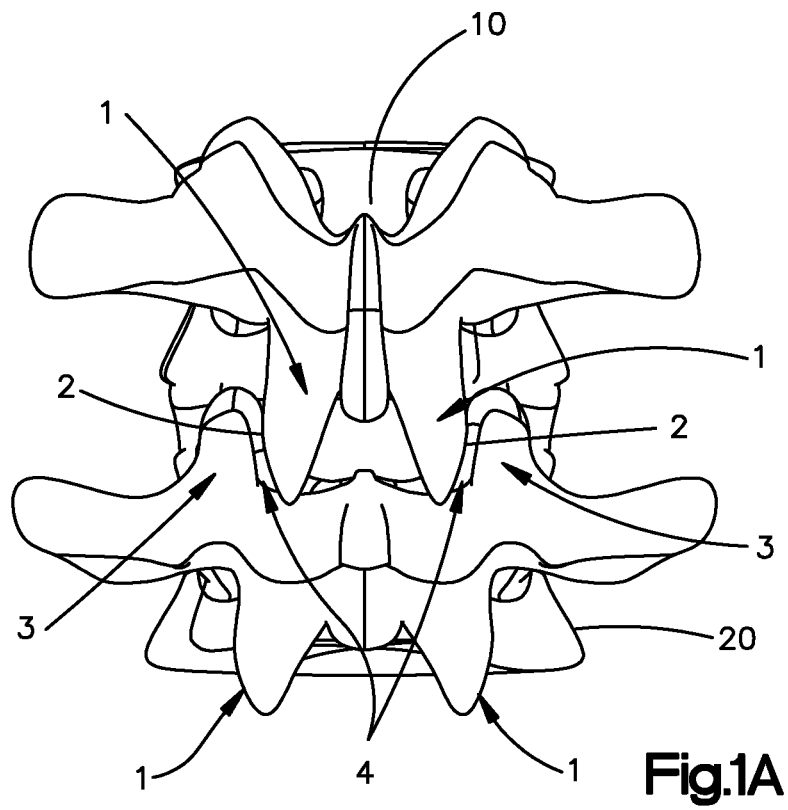
FIG. 1A illustrates a posterior elevational view of a patient's spinal motion segment.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the facet interference screw and designated parts thereof. The words, "anterior", "posterior", "superior", "inferior", "lateral", "sagittal", "axial", "coronal" and related words and/or phrases designate preferred positions and orientations in the human body to which reference is made and are not meant to be limiting. The terminology includes the above-listed words, derivatives thereof and words of similar import.

As described in greater detail below, and as will be appreciated by those skilled in the art, the various embodiments of the present invention provide methods of facet joint augmentation using hydrogels or similar materials and instruments and materials for such procedures.

Certain embodiments of the present invention will now be discussed with reference to the aforementioned figures, wherein like reference numerals refer to like components. Preferred embodiments of the present invention are directed to an exemplary method for facet joint augmentation using a flowable material such as, for example, a hydrogel or similar type materials.

Figure 1B:
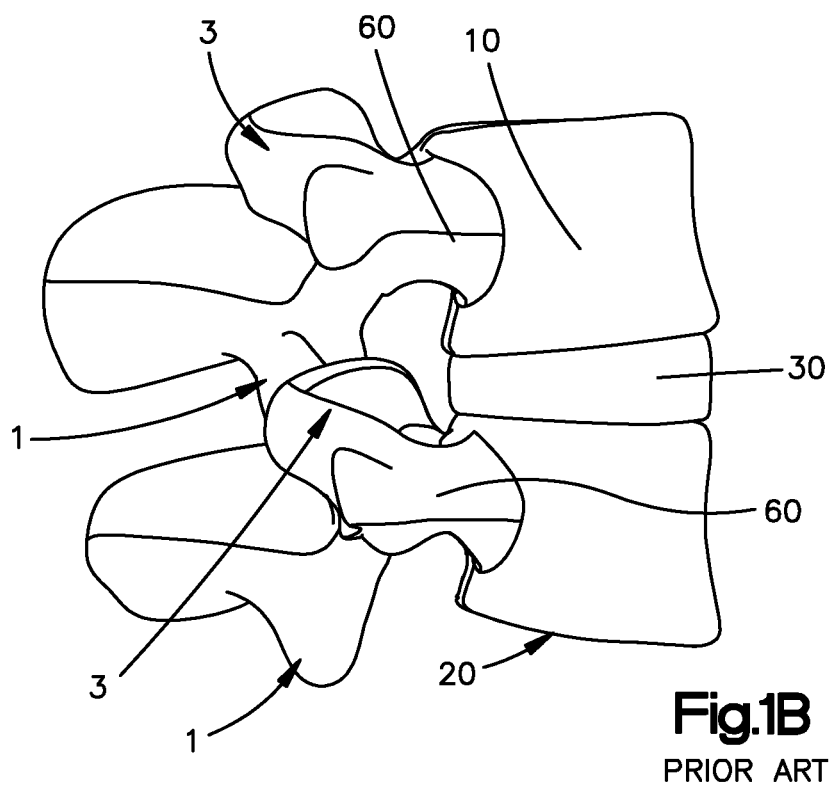
FIG. 1B illustrates a lateral elevational view of a patient's spinal motion segment.
Figure 2:
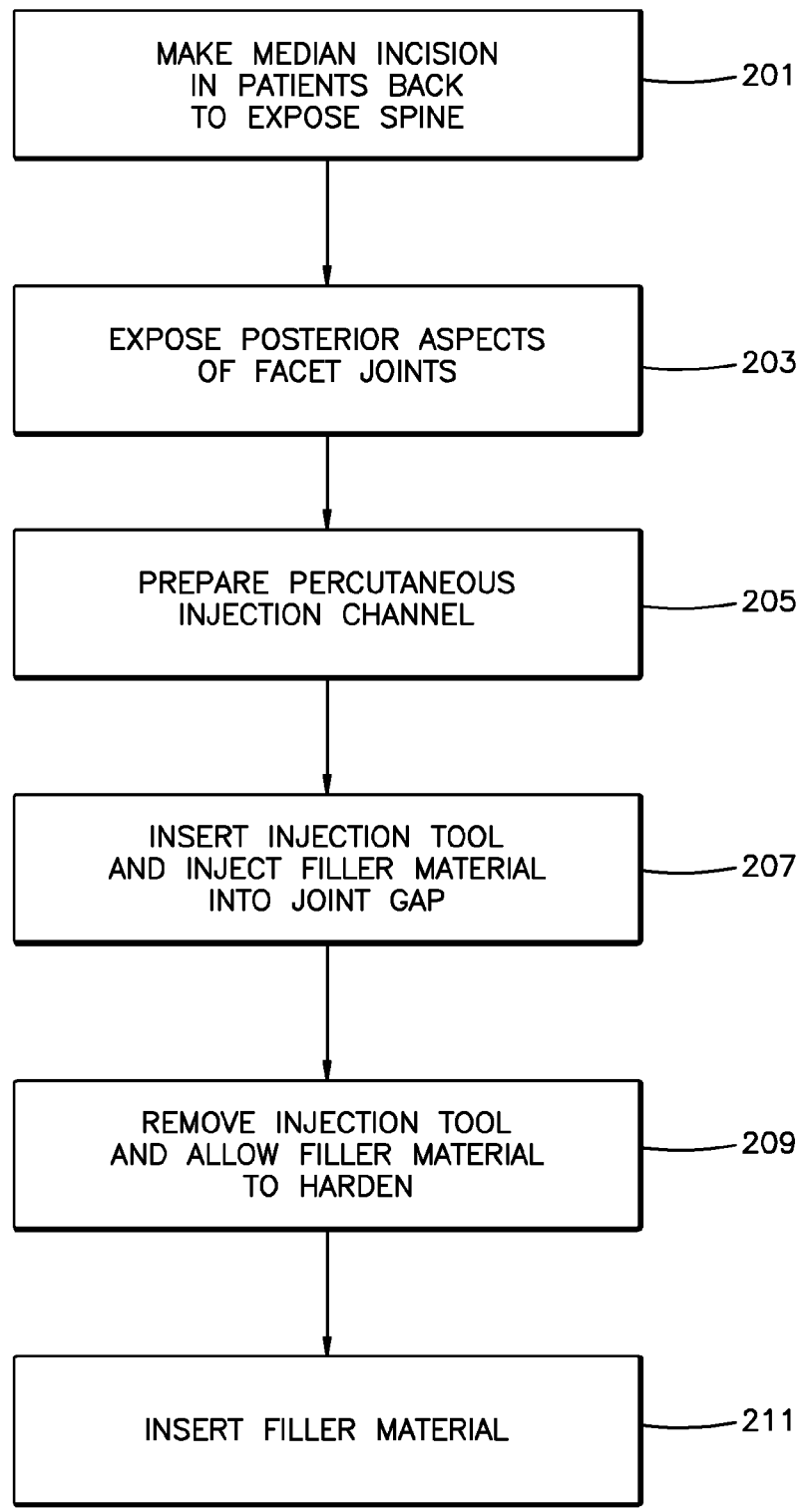
FIG. 2 is a flowchart depicting a method according to a preferred embodiment of the present invention.

Referring to FIGS. 1A and 1B, two exemplary spinal motion segments of the vertebrae in the lumbar region of a patient's spine are shown. The spinal segment includes a superior vertebral body 10, an inferior vertebral body 20 and an intervertebral disc 30. Each of the superior vertebral body 10 and inferior vertebral body 20 include a pair of facet joints 1 that include a superior articulation facet surface 3 and an inferior articulation facet surface 2 respectively. The inferior facet surface 2 of the superior vertebral body 10 and the superior facet surface 3 of the inferior vertebral body 20 are movably interconnected via a joint capsule or facet joint space 4 that guides and limits motion of the motion segment. The joint capsule 4 typically provides a fluid-filled gap between the inferior facet surface 2 and the superior facet surface 3. As a result of natural or traumatic degeneration of the spine, damage to facet joints 1 may cause limited fluid in the facet joint space 4 or other damage. For example, an inflammatory reaction may occur when the cartilaginous surfaces of the facet joint space 4 are degraded, which may lead to direct contact between the inferior facet surface 2 resulting in pain in the facet joints 1.

Augmentation of the facet joints 1 to alleviate pressure on the painful area has been achieved in the past via the insertion of an implant, such as a facet interference screw (not shown). An exemplary facet interference screw and a surgical method of insertion of the same is disclosed in International Application No. PCT/US2009/036175, entitled "Facet Interference Screw", the entirety of which is incorporated herein by reference.

Figure 3:
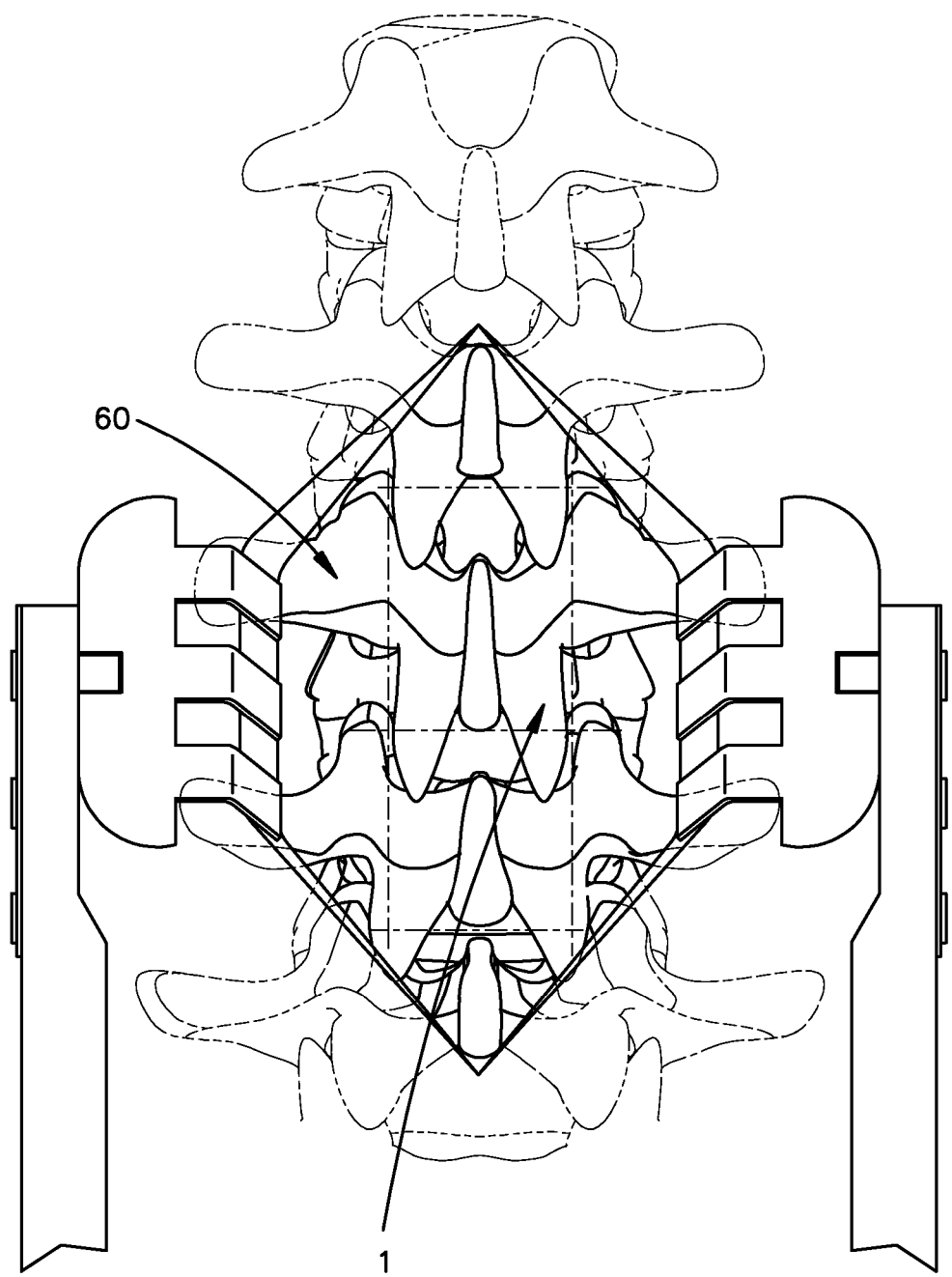
FIG. 3 illustrates a posterior elevational view into an incision where the pedicles and facets are exposed according to the preferred embodiment of FIG. 2.

Preferred methods of facet joint augmentation using hydrogels or similar materials will now be described with reference to FIGS. 1-7C. In order to carry out augmentation of the facet joint 1, a surgeon gains access to the posterior aspects of a patient's spine. To accomplish this, a median incision is preferably made in the patient's back to expose the patient's spine (Step 201). The posterior aspects of an afflicted spinal motion segment and the related facet joints 1 are preferably exposed (Step 203). During the approach to the posterior aspect of the patient's spine a subperiosteal dissection is preferably performed. Once the dissection is performed, the pedicles 60 and facet joint(s) 1 of the patient's spine are preferably exposed, as is best shown in FIG. 3. This incision and dissection can be performed using any heretofore known or hereafter developed techniques.

Figure 4:
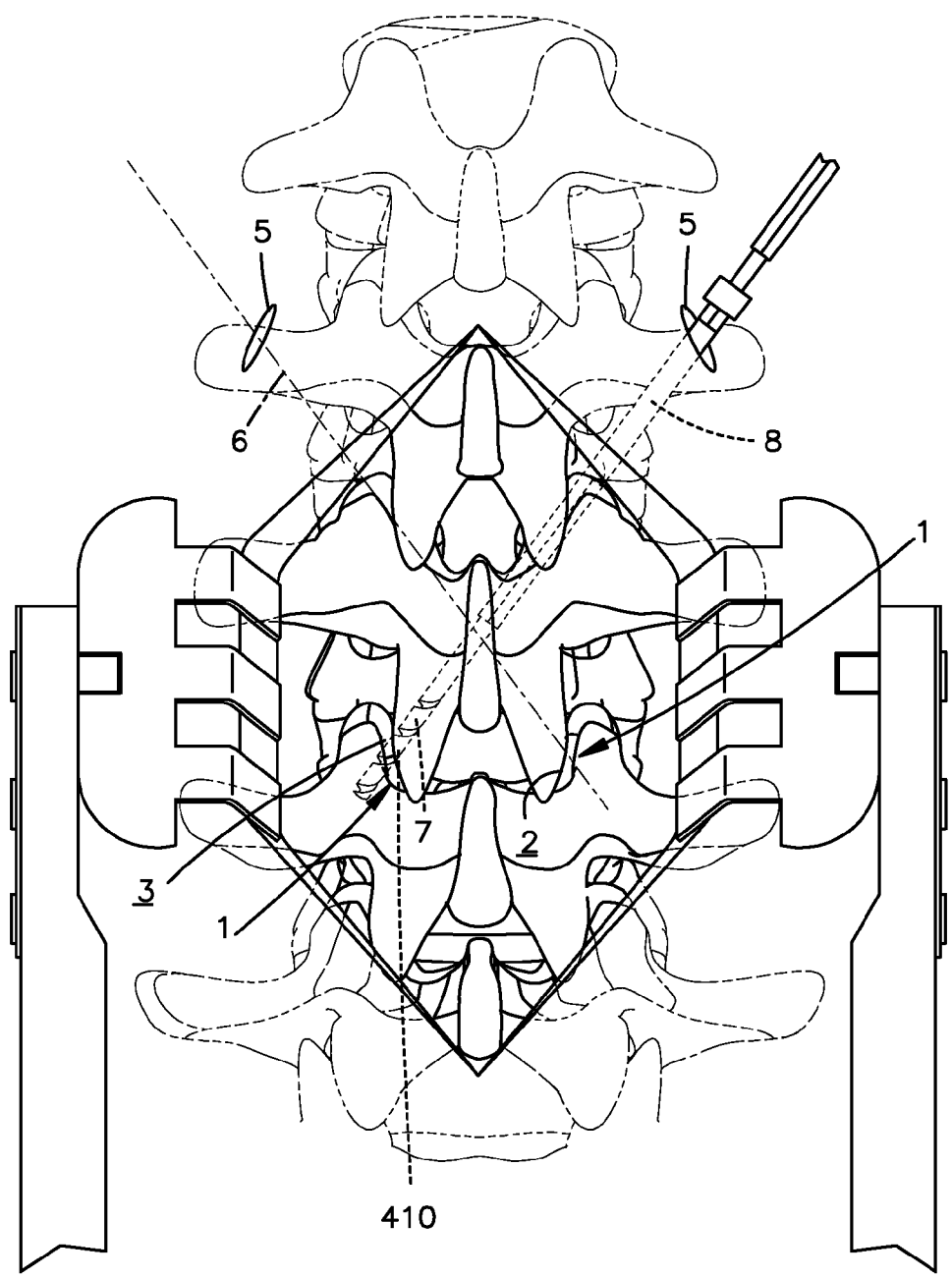
FIG. 4 illustrates a posterior elevational view showing the preparation of two injection channels through two percutaneous incisions according to the preferred embodiment of FIG. 2.

Once the facet joints 1 have been exposed, the surgeon preferably creates a postero-lateral incision(s) 5 in the patient's skin as can be seen in FIG. 4. Through the incision 5, a percutaneous injection channel 6 is preferably prepared, for example by the percutaneous insertion of a drill bit or an awl 410 as a cortical bone opening instrument. The channel 6 may be made by any heretofore known or hereafter developed conventional surgical technique for drilling through a bony structure such as a vertebra. Using this technique, the injection channel 6 is preferably opened through the laminae and through the inferior facet articulation surface 2. The channel 6 preferably terminates before breaching the superior facet articulation surface 3 (Step 205). The channel 6 preferably allows the insertion of the hydrogel or similar material without damaging the superior facet articulation surface 3. Once the injection channel 6 has been created, the drill bit 410 is removed leaving an open channel 6 through which an injection tool or instrumentation 9 is inserted into channel 6. An image intensifier tool (e.g., Fluoroscopy not shown) may be used to guide and monitor the drill bit 410 while the channel 6 is formed so that the drill bit 410 does not penetrate the superior facet articulation surface 3. However, the surgeon may utilize the drill bit 410 to form the channel 6 without use of Fluoroscopy using tactile feedback and may create a small divot or gouge in the superior facet surface without compromising the preferred surgical technique. Additionally, a drill sleeve 8 can be used protect the surrounding soft tissue from winding about the drill bit 410 when the channel is created.

As can be seen in FIG. 5, once the channel 6 is formed, an injection tool 9, which is preferably loaded with a joint gap filler material 50 (such as a hydrogel or similar material as discussed in more detail below), is inserted though the channel such that ejection ports 9b are in the facet joint gap 4. Once ejection ports 9b are positioned in the facet joint gap 4, the joint gap filler material 50 is injected into the facet joint gap 4 while leaving the facet capsule completely intact (Step 207). The joint gap filler material 50 is then allowed to harden or polymerize thereby filling the facet joint gap. An image intensifier tool (e.g., Fluoroscopy) may be used to guide and monitor the injection tool 9 so that a preferred blunt tip 9c of the injection tool 9 reaches the facet joint gap 4 and the gap filler material 50 is injected properly.

Figure 7C:
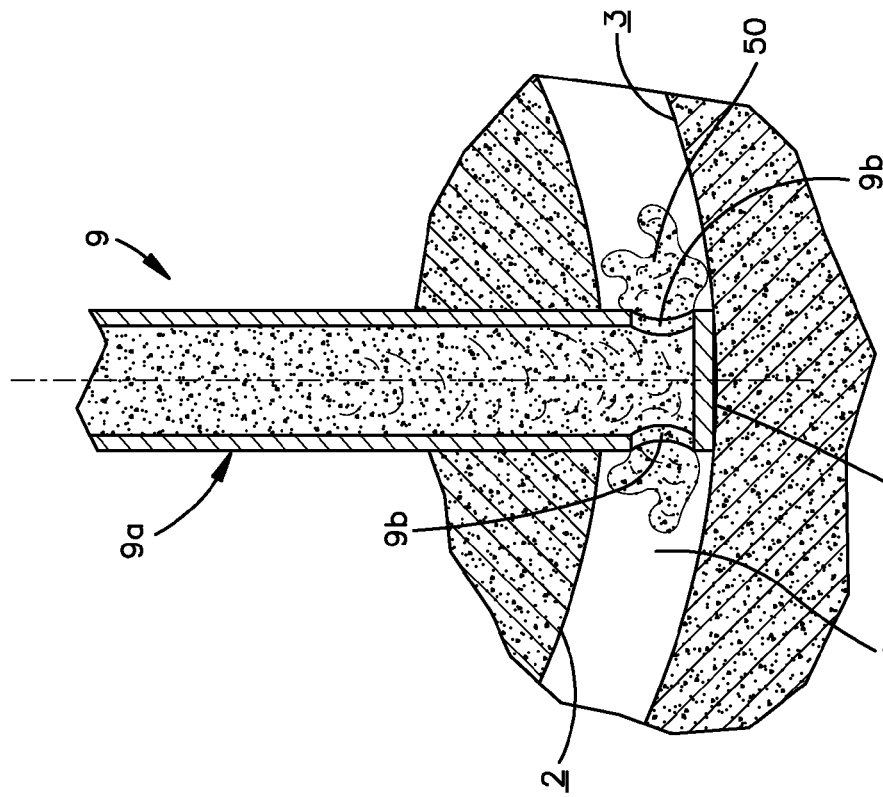
FIG. 7C is a cross-sectional view of the injection body of FIG. 7A, taken along line 7B-7B of FIG. 7A and positioned in a facet joint space.
Figure 7B:
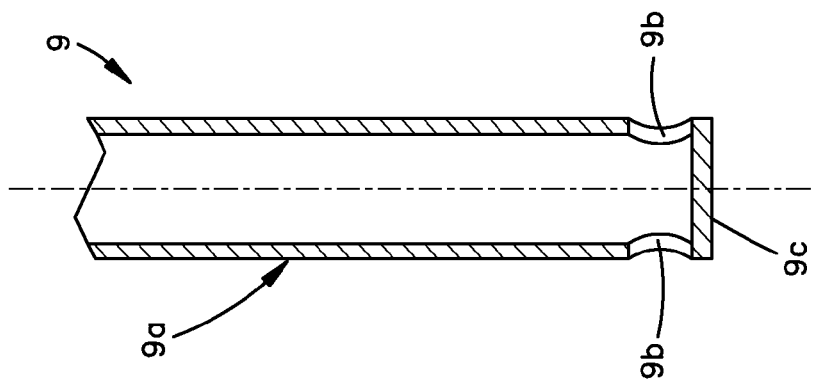
FIG. 7B illustrates a cross-sectional view of the injection body of FIG. 7A, taken along 7B-7B of FIG. 7A.
Figure 7A:
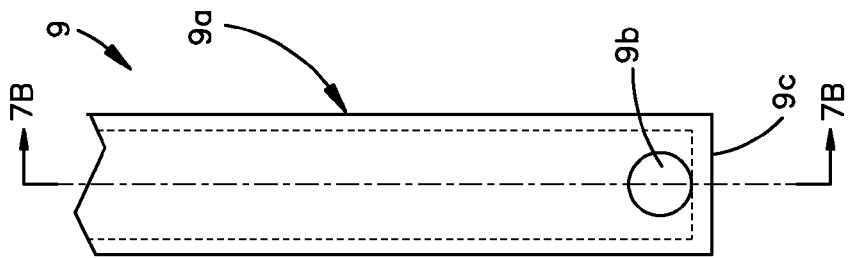
FIG. 7A is a side elevational view of an injection body in accordance with the preferred embodiment of the present invention.

The injection tool 9 can be any conventional tool now or hereafter known in the art to inject fluid material within a bony structure such as a vertebra including for example a conventional push rod or plunger type tool. As can be seen in FIGS. 7A-7C, the injection tool 9 includes an injection body 9a with the blunt tip 9c, and the one or more radially located side-opening ejection ports 9b. The ejection ports 9b release the gap filler material 50 into the facet joint gap 4. The distal tip 9c of the injection body 9a preferably forms and encloses the ejection ports 9b. The blunt tip 9c is configured to ensure that even if injection tool 9 comes in contact with the superior facet articulation surface 3, the superior facet articulation surface 3 is typically not damaged.

Once the filler material 50 has been injected, the injection tool 9 is removed leaving the filler material 50 in the joint capsule 4 to solidify or polymerize (Step 209). In the preferred embodiment, the injection tool 9 is removed prior to hardening of the filler material 50 such that no cutting instrument is necessary to dislodge the injection tool 9 from the polymerized filler 50. If the filler material 50 has already hardened, the injection tool 9 can be dislodged from the hardened material using conventional cutting techniques.

Once the filler material 50 has hardened, the filler material 50 may be pressurized, or at least maintained under pressure, by preferably inserting a sealing member 51 into the access channel 6 to seal the channel against leakage of the material 50. The injection channel 6 through the lamina is preferably sealed in order to re-establish the boney integrity of the concerned lamina(e). The sealing member 51 may be a plug of bone cement that is advanced into the access channel 6 to exert an appropriate pressure on the filler material 50 implanted in the facet joint gap 4. As can be seen in FIG. 6, the sealing member 51 is inserted through access channel 6 using a simple instrument such as a push rod or plunger-type tool 52 to urge sealing member 51 toward the distal end of the access channel 6, such that the distal end 51a of the sealing member 51 is positioned close to the superior facet articulation surface 3 (Step 211). An exemplary method of implanting and inserting a sealing member to seal implanted material is disclosed in U.S. patent application Ser. No. 12/163,407, entitled "Supplementation or Replacement of a Nucleus Pulposus of an Intervertebral Disc", the entirety of which is incorporated herein by reference. The delivery instrument 52 is then removed and the surgical site is closed by conventional procedures.

In the preferred embodiment, the sealing member 51 is a cylindrically-shaped bone plug 51 and is characterized by a diameter similar or equal to the diameter of the access channel 6. In other configurations, the bone plug 51 is formed from allograft bone or bone substitute such as, for example, hydroxyapatite or tri-calcium phosphate, although any biocompatible material composition can be utilized such as, for example, ceramics, titanium, stainless steel, PEEK, other plastics, or other biocompatible materials now or heretofore known in the art. The sealing member 51 may also be comprised of an injectable material that is injected in flowable form into the channel 6 so that when the liquid hardens, the solid material fills the channel 6 itself. Alternatively this can be accomplished through the process of maceration to soften the surrounding tissue. When the sealing member 51 is formed of bone material, the bone can be allograft bone that is partially demineralized, fully demineralized, or nondemineralized. Further, the bone material can be autograft or xenograft bone that is harvested from the drilling process described above and preformed into the shape of the plug 51. The bone plug 51 can be threaded or include surface texture features to reduce the likelihood of expulsion from the channel 6.

Throughout the implantation method, the facet capsule 4 is preferably left intact and, therefore, the likelihood of leakage of the filler material 50 within the spinal motion segment is reduced or eliminated. The soft material of the facet gap filler 50 re-establishes the facet joint 1 and relieves the stress on the superior facet articulation surface 3 and the inferior facet articulation surface 2 which may be damaged due to an arthritic condition of the facet joint 1. This procedure also improves lubrication, enables fluid exchange with the surrounding cartilage and subchondral surfaces, and prevents contact between the facet joint articulation surfaces 2, 3 to reduce or eliminate irritation and inflammatory responses due to bone on bone contact. Due to the preferred soft and elastic properties of the facet gap filler 50, mobility of the motion segment is preferably restored. Further, the preferred low modulus characteristics of the filler material 50 mimic the properties of healthy cartilage such that the desirable local properties and stresses are maintained or restored.

The joint gap filler material 50 may be any biocompatible material now or hereafter known for such purpose including, but not limited to, saline, air, gas, water, any of the family of injectable in-situ curing polymers now or hereafter used in the body, such as, for example, polyurethanes, silicones, or hydrogels.

For example, the filler material 50 may be a low modulus elastomer that can include hydrogels, ionomers, silicones or thermoplastic resins that are injected as a fluid and polymerize, cure or hardens in situ, (e.g., after approximately five to twenty 5-20 minutes). A range of biocompatible hydrogel materials, however, can also be used as the joint gap filler material 50 including, for example, polyvinyl alcohol, polyacrylic acid, acrylate polymers and copolymers with an abundance of hydrophilic groups, p-vinyl pyrollidone, polyethyleneimine. Additionally, setting or curing hydrogel based copolymer groups including polyethyleneimine, poly(diethylaminoethyl methacrylate), poly(ethylaminoethyl methacrylate or thermally setting hydrogels based upon the copolymers of poly-N-isopropylacrylamide with polyethylene glycol, copolymers of polyethylene oxide and polyphenylene glycol and polylactides may be used. In certain embodiments, ionic setting hydrogels based upon the polymers of ethylacrylate, methacrylic acid and 1,4-butanediacrylate are used as the filler material 50. In addition, non-resorbable long fibers such as ultra-high molecular weight polyethylene (UHMWPE), carbon, etc., that can be injected could be employed.

Alternatively, the filler material 50 may be a thermoplastic polymer such as polyesterurethane, polyetherurethanes, polycarbonateurethanes (PCU), polycarbonateurethane-silicone copolymer or polycarbonateurethane modified with surface modifying end groups such as, for example, silicone or fluorocarbon end groups, RTV curing silicones based upon a polydimethylsiloxane incorporating a range of catalysts to provide in situ, fast cure, etc.

The filler material 50 is preferably injected in a flowable state and takes on a semi-rigid hardness or green strength upon curing in its implanted state. For example, the filler material 50 may be a thermogelling transforming polymer, a phase transforming polymer or a thermo-setting polymer with a variety of moduli. The utilization of such polymers to fill the facet joint gap 4 enables the surgeon to optimize his/her particular application by varying the properties of the cured polymer to possess structural properties similar to the natural physiology of the patient. U.S. patent application Ser. No. 10/837,082, entitled "Thermogelling Polymer Blends for Biomaterial Applications", which is hereby incorporated by reference in its entirety and discloses a thermogelling material in the form of a PniPaam copolymer that transitions slightly below body temperature into an elastic solid.

Additional filler materials that may be used including for example, ultraviolet (UV) curable materials and other cross linking chemistries such as polymethylmethacrylate curing bone cements. UV curing materials are typically acrylates or methacrylates. In use, UV curing materials can be injected into the facet joint gap 4 and, when the facet joint gap 4 is at the desired fill pressure or volume, a UV light source can be used to initiate the curing reaction to form the final polymer material. In addition, different monomeric materials can be used to tailor the mechanical properties of the filler material 50. Because the reaction can be initiated at the surface and propagate inward, the risk of leaching of unreacted components is generally limited as the material 50 proximate to the opening of the channel 6 at the inferior facet surface 2 is the first material to cure and harden.

Other cross linking chemistries include the use of amine containing polymers and/or monomers that could be reacted by the addition of aldehyde containing materials. The aldehyde/amine reaction is used to generally crosslink materials for various applications.

Furthermore, for radiographic visualization, the filler material 50 may also incorporate radiopaque materials so that the filler material 50 can be visualized radiographically after implantation. Alternatively, the injection tool 9 can incorporate one or more radiopaque markings (not shown) of known position to facilitate surgical placement and positioning via radiographic visualization.

The maintenance of intact facet joints 4 reduces or eliminates the potential for blood and fluids to enter the facet capsule and initiate inflammatory reactions. Elimination of blood from the facet capsule also prevents spontaneous fusion of the facet joints 4. The surgical intervention has a very low impact and can be accommodated in a minimally invasive manner to thereby avoid spreading the spinal processes or lamina(e). Further, due to the preferred quick curing or setting time characterizing the filler material 50 and the minimally traumatic surgical procedure provided by the present system and method, it is envisioned that the patient can be mobilized shortly following the operation.

Those skilled in the art will recognize that the method and system of the present invention has many applications, may be implemented in many manners and, as such is not to be limited by the foregoing embodiments and examples. Any number of the features of the different embodiments described herein may be combined into one single embodiment and alternate embodiments having fewer than or more than all of the features herein described are possible. Functionality may also be, in whole or in part, distributed among multiple components, in manners now known or to become known. Moreover, the scope of the present invention covers conventionally known and features of those variations and modifications through the components described herein as would be understood by those skilled in the art. It is the intention, therefore, to be limited only as indicated by the scope of the claims appended hereto.

It is also to be understood that the following claims are intended to cover all of the generic and specific features of the invention herein described and all statements of the scope of the invention, which, as a matter of language, might be said to fall therebetween.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method for augmenting a facet joint, the method comprising the steps of:
    (a) exposing the posterior aspects of a spinal motion segment in a first incision;
    (b) preparing an access path through a separate postero-lateral percutaneous incision using a drilling instrument that traverses through at least a portion of the lamina and an inferior facet articulation surface, and terminates within the facet joint gap;
    (c) inserting an injection instrument through the access path;
    (d) injecting augmentation filler into the facet joint gap in a liquid state;
    (e) removing the injection instrument; and
    (f) inserting a sealing material through the access path such that the terminal end of the sealing material is positioned generally coplanar with the inferior facet articulation surface.

2. The method of claim 1 wherein the augmentation filler is selected from the group comprised of hydrogels, ionomers, silicones or thermoplastic resins.

3. The method of claim 1 wherein step (d) further comprises the step of:
    (d1) utilizing an image intensifier tool to enable proper insertion of the injection instrument.

4. The method of claim 1 wherein the sealing material is a bone plug.

5. The method of claim 4 wherein the bone plug is selected from the group consisting of allograft bone, hydroxyapatite or tri-calcium phosphate.

6. The method of claim 4 wherein the bone plug is cylindrical in shape and has a similar diameter to the diameter of the access path.

7. The method of claim 1 comprising the further step of:
    (g) pressurizing the augmentation filler of step (d) by the insertion of the sealing material of step (f).

8. The method of claim 1 wherein the injection instrument contains a blunt tip at its distal end.

9. A method for augmenting a facet joint, comprising the steps of:
    (a) creating a first incision in a patient's back that exposes the posterior aspects of a spinal motion segment;
    (b) creating a separate postero-lateral percutaneous incision to allow insertion of a drilling instrument;
    (c) preparing an access path through the separate postero-lateral percutaneous incision using the drilling instrument which access path traverses through at least a portion of the lamina and an inferior facet articulation surface, and terminates within the facet joint gap;
    (d) inserting an injection instrument with augmentation filler through the access path;
    (e) injecting the augmentation filler into the facet joint gap;
    (f) removing the injection instrument; and
    (g) inserting a sealing member through the access path such that the sealing member maintains pressure on the augmentation filler.

10. The method of claim 9 wherein the augmentation filler is selected from the group comprised of hydrogels, ionomers, silicones or thermoplastic resins.

11. The method of claim 9 wherein step (d) further comprises the step of: (d1) utilizing an image intensifier tool to enable proper insertion of the injection instrument.

12. The method of claim 9 wherein the sealing material is a bone plug.

13. The method of claim 12 wherein the bone plug is selected from the group consisting of allograft bone, hydroxyapatite or tri-calcium phosphate.

14. The method of claim 12 wherein the bone plug is cylindrical in shape and has a similar diameter to the diameter of the access path.

15. The method of claim 9 wherein the injection instrument contains a blunt tip at its distal end.

* * * * *